United States Patent
Gatineau et al.

(10) Patent No.: US 8,557,339 B2
(45) Date of Patent: Oct. 15, 2013

(54) METHOD FOR THE DEPOSITION OF A RUTHENIUM CONTAINING FILM

(75) Inventors: Julien Gatineau, Ibaraki (JP); Christian Dussarrat, Wilmington, DE (US)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 760 days.

(21) Appl. No.: 12/520,116

(22) PCT Filed: Dec. 20, 2007

(86) PCT No.: PCT/IB2007/055258
§ 371 (c)(1),
(2), (4) Date: Oct. 6, 2009

(87) PCT Pub. No.: WO2008/078295
PCT Pub. Date: Jul. 3, 2008

(65) Prior Publication Data
US 2010/0034971 A1   Feb. 11, 2010

(30) Foreign Application Priority Data

Dec. 22, 2006   (EP) .................................... 06301291

(51) Int. Cl.
*C23C 16/18*   (2006.01)
(52) U.S. Cl.
USPC .................. 427/250; 427/255.31; 117/84
(58) Field of Classification Search
USPC ................. 427/250, 255.31; 117/84
See application file for complete search history.

(56) References Cited

U.S. PATENT DOCUMENTS

| | | | |
|---|---|---|---|
| 5,962,716 A | 10/1999 | Uhlenbrock et al. | |
| 6,420,582 B1* | 7/2002 | Okamoto | 556/136 |
| 6,517,616 B2 | 2/2003 | Marsh et al. | |
| 6,753,245 B2* | 6/2004 | Choi | 438/613 |
| 6,897,160 B2 | 5/2005 | Derderian et al. | |
| 7,667,065 B2* | 2/2010 | Thompson | 556/136 |
| 7,722,926 B2* | 5/2010 | Cho et al. | 427/255.28 |
| 2001/0036509 A1* | 11/2001 | Kitada et al. | 427/255.28 |
| 2002/0004293 A1* | 1/2002 | Soininen et al. | 438/584 |
| 2002/0065427 A1* | 5/2002 | Okamoto | 556/136 |
| 2003/0073860 A1* | 4/2003 | Choi | 556/10 |
| 2006/0024190 A1 | 2/2006 | Kelly | |
| 2008/0171436 A1* | 7/2008 | Koh et al. | 438/681 |
| 2008/0268151 A1* | 10/2008 | Choi | 427/250 |
| 2009/0205538 A1* | 8/2009 | Thompson et al. | 106/287.18 |
| 2011/0224453 A1* | 9/2011 | Furukawa et al. | 556/136 |

FOREIGN PATENT DOCUMENTS

| | | |
|---|---|---|
| JP | 09 235287 | 9/1997 |
| JP | 2002-114795 | * 4/2002 |
| JP | 2003 533535 | 11/2003 |
| JP | 2003 342286 | 12/2003 |
| JP | 2004 292332 | 10/2004 |
| JP | 2005 60814 | 3/2005 |
| WO | WO 01 87991 | 11/2001 |
| WO | WO 2005 10331 B | 11/2005 |

OTHER PUBLICATIONS

Smith, K.C., et al., "Evaluation of precursors for chemical vapor deposition of ruthenium". Thin Solid Films 376 (2000) pp. 73-81.*
Kirss, Rein U., "Synthesis, characterization and spectroscopy of alkyl substituted edge-bridged open ruthenocenes". Inorganica Chimica Acta, 357 (2004) 3181-3186.*
International Search Report for PCT/IB2007/055258.
Neto, C.C., et al. "Double nucleophilic addition of carbon donors to [(benzene)(arene)ruthenium]2+cations." Journal of the Chemical Society, Chemical Communications, Chemical Society. Letchworth, GB, No. 23, 1990, pp. 1703-1704.
Kirss, R.U., et al. "Synthesis, characterization and spectroscopy of alkyl substituted edge-bridged open ruthenocenes." Inorganica Chimica Acta, vol. 357, No. 11, 2004, pp. 3181-3186.
Gregorcyzk, K. et al., "Atomic Layer Deposition of Ruthenium Using the Novel Precursors bis(2,6,6-trimethyl-cyclohexadienyl)ruthenium," Chemistry of Materials (2011) 23(1), pp. 2650-2656.
Gregorczyk, K. et al., "Conduction in ultrathin ruthenium electrodes prepared by atomic layer deposition," Materials Letters 73 (2012), pp. 43-46.
Kirss, R.U. et al., "Synthesis, characterization and electrochemistry of bis(3-aryl-6,6-dimethylcyclohexadlenyl)ruthenium complexes," Inorganica Chimica Acta 359 (2006), pp. 4393-4397.
Müller, J. et al., "Kationische π-Olefin-Ruthnium-Komplexe," Jouranl of Organometallix Chemistry, 97 (1975), pp. 275-282.
Yoder, C.H. et al., "NMR Spectra and Basicities of Haloalkylsiyl Amines," Journal of of Organometallic Chemistry, 233 (1982), pp. 275-279.
Written Opinion for corresponding PCT/IB2007/055258, Apr. 4, 2008.
Song, Y.W. et al., "Atomic layer deposition of Ru by using a Ne Ru-precursor," ECS Transactions, 2 (4) 2006, pp. 1-11.
Shibutami, T. et al., "A novel ruthenium precursor for MOCVD without seed ruthenium layer," Tosoh R&D Review, 47, 2003, pp. 61-64.

* cited by examiner

Primary Examiner — Bret Chen
(74) Attorney, Agent, or Firm — Patricia E. McQueeney

(57) ABSTRACT

Disclosed are processes for depositing ruthenium containing films on substrates using an organometallic compound having the following formula:

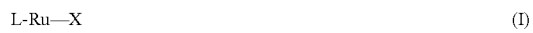

Figure 1:
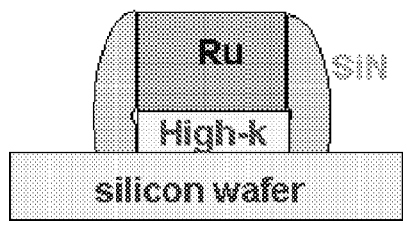

wherein L is a non-aromatic cyclic unsaturated hydrocarbon ligand (L), having at least six cyclic carbon atoms, said cycle being unsubstituted or substituted, and X is either a non aromatic cyclic unsaturated hydrocarbon ligand identical or different from (L), having at least six cyclic carbon atoms said cycle being unsubstituted or substituted or a cyclic or acyclic conjugated alkadienyl hydrocarbon ligand having from five to ten carbons atoms, said hydrocarbon ligand being unsubstituted or substituted.

11 Claims, 1 Drawing Sheet

METHOD FOR THE DEPOSITION OF A RUTHENIUM CONTAINING FILM

This application is a 371 of International PCT Application PCT/IB2007/055258, filed Dec. 20, 2007, the entire contents of which are incorporated herein by reference.

The present invention concerns organometallic compounds based on Ruthenium, the process of their deposition on a substrate and their use in the semi-conductor industry and the like.

Ruthenium (Ru) is expected to be used in the industrial semiconductor manufacturing process for many applications in the coming years. This move towards the use of new materials for chip manufacturing is necessary to solve issues generated by the continuous scaling trend imposed to the industry. For the next generation nodes, Ru is considered as the best candidate for the electrode capacitor for FeRAM and DRAM applications. Ru has the required properties, such as a high melting point, a low resistivity, a high oxidation resistance and adequate work functions, making it as a potential gate electrode material for CMOS transistor. In fact, the resistivity of Ru is lower than the resistivities of Iridium (Ir) and of platinum (Pt), and it can be easier used in dry etching. Additionally, Ruthenium oxide ($RuO_2$) and Strontium Ruthenium Oxide (SRO, $SrRuO_3$), that have a high conductivity and can be formed by diffusion of oxygen that could come from ferroelectric films such as Lead-Zirconate-Titanate (PZT), Strontium Bismuth Tantalate (SBT) or Bismuth Lanthanum Titanate (BLT), will have less impact on electrical properties than other metal oxides known to be more insulating.

Ru is also a promising Back End Of Line (BEOL) process candidate as a liner material for copper. A single Ru film would replace the Ta, Ta(Si)N, and the copper seed layer. A Ru process would replace the two steps Ta/Ta(Si)N process with a single step.

A large variety of Ru CVD (chemical vapor deposition) precursors, are available and many have been studied. However, the currently available precursors have a low vapor pressure (i.e. 0.1 Torr at 73° C. for $Ru(EtCp)_2$). The Ru films obtained with these known precursors contain significant amounts of carbon and oxygen impurities. The carbon impurities are suspected to come from the precursor material. The oxygen impurities come from the co-reactant gas ($O_2$). It is known from T. Shibutami et al. (Tosoh R&D Review, 47, 2003), that Ru films have a poor adherence, are not uniform and also have a characteristically long incubation time (The incubation time is defined as the time required for the deposition to effectively start, i.e. by the difference time between the moment when the gas is flown in the reaction furnace and the moment when the film grows).

It is known from U.S. Pat. No. 6,897,160, to use Ru precursors, such as tricarbonyl(1,3-cyclohexadiene) Ru precursor, to deposit rough ruthenium oxide layers, wherein said particular precursor (see example 4 of said patent) is held in a bubbler reservoir at room temperature (about 25° C.) and helium is bubbled through it.

However, it is also known from U.S. Pat. No. 6,517,616 and from U.S. Pat. No. 5,962,716 that $Ru(CO)_3$ (1,3-cyclohexadiene) product is not liquid at room temperature and that it is necessary to dissolve it to obtain a liquid solution of precursor and solvent through which the inert gas such as helium is bubbled $Ru(CO)_3$(1,3-cyclohexadiene) is also disclosed also in the article of Y. W. Song et al. (ECS transactions, 2(4), 1-11, 2006), including its solid nature at ambient temperature, with a melting point of 35° C.

All the known CO containing Ru precursors have essentially the same drawback, which is their high melting point. A solvent is therefore necessary to obtain a liquid product that allows to flow more easily vapors of the precursor to the reaction furnace by regular liquid delivery methods such as bubbling or vaporization methods.

However, the use of a solvent is usually viewed as having a bad influence on the deposition process due to the intrusion of the solvent molecules in the reactor and the incorporation of undesired impurities in the deposited films. Moreover, the solvents used are usually toxic and/or flammable and their usage brings many constraints (safety aspects, environmental issues). Besides, the use of precursors with melting points higher than 20° C. (and even for those having a melting point above 0° C.) implies many additional constraints during the process deposition (heating of the delivery lines to avoid condensation of the precursor at undesired locations) and during the transportation.

The reactivity of the known CO containing precursors does not enable today to reach an atomic layer deposition (ALD) regime. Ruthenium films are only deposited by CVD and some articles even outline that ALD mode is not possible with the $Ru(CO)_3$(1,3-cyclohexadiene) precursor. ALD is a deposition technique that is widely used nowadays for its capability of depositing uniform and conformal thin films thanks to the chemisorption of one reactant on a surface that was saturated with another co-reactant, and vice versa. It implies a sequential introduction of the reactants in the reaction furnace, each reactant introduction step being separated by a purge of the reaction furnace by an inert gas mixture. A Ruthenium deposition in ALD mode can consist for instance of a period of purge, which is followed by the introduction of vapors of the ruthenium precursor. The vapors of the precursor will uniformly adsorb on the substrate and a layer of approximately one atom is formed. Once this layer is formed, no ruthenium atoms can react with the new surface of the substrate. This is called the self-limiting property of ALD. Then, an inert gas is flowed into the reaction furnace in order to get rid of the un-reacted precursor molecules and all the generated by-products. A co-reactant is introduced in order to react with the previously deposited layer and the resulting material is a ruthenium film. This 4 step-process is called a cycle and this cycle can be repeated as needed, until the desired thickness of ruthenium is obtained, knowing that in an ideal ALD regime, 1 cycle enables to deposit a layer of 1 atom of Ruthenium.

The objective of the invention was thus to develop new organo-Ruthenium compounds, which have an improved thermal stability, which can be more easily handled and used, which allow depositing films by CVD, ALD or any other deposition techniques, which enables to deposit films with a shorter incubation, which limit the formation of an oxide layer at the interface with the sub-layer, said oxide layer generating undesired properties.

Low Deposition Temperature of the Ruthenium Films

Another objective of the invention was to provide organo ruthenium compounds which are liquid at room temperature, which can be provided as pure liquids, without the addition of a solvent, which enables the deposition of pure ruthenium films or ruthenium containing films depending on the co-reactant used with the precursor, whose resulting films are deposited without detectable incubation time, and for which an ALD regime can be obtained for pure ruthenium deposition as well as for deposition of other ruthenium containing films ($SrRuO_3$, $RuO_2$ for example).

That is why, according to a first embodiment, the invention relates to an organo-metallic compound of the formula (I):

L-Ru—X    (I)

wherein:

L is a non-aromatic cyclic unsaturated hydrocarbon ligand (L), having at least six cyclic carbon atoms, said cycle being unsubstituted or substituted by one or more substitution groups selected from linear or branched alkyl groups having from one to six carbon atoms, unsubstituted or substituted by one or more radicals selected from fluoro, hydroxy or amino, linear or branched alkylamide groups having from one to six carbon atoms, linear or branched alkoxy groups having from one to six carbon atoms, linear or branched alkyl amidinates having from one to six carbon atoms, and X is either a non aromatic cyclic unsaturated hydrocarbon ligand identical or different from (L), having at least six cyclic carbon atoms said cycle being unsubstituted or substituted by one or more substitution groups selected from linear or branched alkyl groups having from one to six carbon atoms unsubstituted or substituted by one or more radicals selected from fluoro, hydroxy or amino, linear or branched alkylamide groups having from one to six carbon atoms, linear or branched alkoxy groups having from one to six carbon atoms, linear or branched alkyl amidinates having from one to six carbon atoms, or a cyclic or acyclic conjugated alkadienyl hydrocarbon ligand having from five to ten carbons atoms, said hydrocarbon ligand being unsubstituted or substituted by one or more substitution groups selected from linear or branched alkyl groups having from one to six carbon atoms unsubstituted or substituted by one or more radicals selected from fluoro, hydroxy or amino, linear or branched alkylamides group having from one to six carbon atoms, linear or branched alkoxy groups having from one to six carbon atoms, linear or branched alkyl amidinates having from one to six carbon atoms.

In the organometallic compound as defined hereinbefore, at least one organic ligand is made of a carbon ring with at least six cyclic carbon atoms, whereas the corresponding π electrons, hereafter called "electronic cloud," form a partially open circle. An example of such a ligand is represented by the following formula:

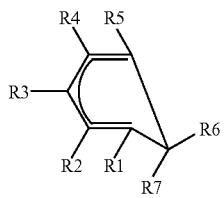

According to a first particular embodiment, the invention is related to the organometallic compound of the formula (I) as defined hereinbefore, wherein (L) is selected from cyclohexadienyl (hereafter chxd, $C_6H_7$) and cycloheptadienyl (hereafter chpd $C_7H_9$) ligands, said ligands being unsubstituted or substituted by one or more substitution groups selected from linear or branched alkyl groups having from one to six carbon atoms unsubstituted or substituted by one or more radicals selected from fluoro, hydroxy or amino, linear or branched alkylamides group having from one to six carbon atoms, linear or branched alkoxy groups having from one to six carbon atoms, linear or branched alkyl amidinates having from one to six carbon atoms, or a cyclic or acyclic conjugated alkadienyl hydrocarbon ligand having from five to ten carbons atoms, said hydrocarbon ligand being unsubstituted or substituted by one or more substituting groups selected from linear or branched alkyl groups having from one to six carbon atoms unsubstituted or substituted by one or more radicals selected from fluoro, hydroxy or amino, linear or branched alkylamide groups having from one to six carbon atoms, linear or branched alkoxy groups having from one to six carbon atoms, linear or branched alkyl amidinates having from one to six carbon atoms.

According to a second particular embodiment, the invention is related to the organometallic compound of the formula (I) as defined hereinbefore, wherein X is selected from cyclohexadienyl (hereafter chxd, $C_6H_7$), cycloheptadienyl (hereafter chpd $C_7H_9$), cyclopentadienyl, pentadienyl, hexadienyl and heptadienyl ligands, said ligands being unsubstituted or substituted by one or more substituting groups selected from linear or branched alkyl groups having from one to six carbon atoms unsubstituted or substituted by one or more radicals selected from fluoro, hydroxy or amino, linear or branched alkylamide groups having from one to six carbon atoms, linear or branched alkoxy groups having from one to six carbon atoms, linear or branched alkyl amidinates having from one to six carbon atoms. When X is an acyclic ligand, it is for example a (1-3η:6-8η)-2,7-dimethyl octadienyl ligand.

According to a third particular embodiment, the invention is related to the organometallic compound of the formula (I) as defined hereinbefore, wherein the substitution groups of the ligands L and X are oxygen-free and more particularly to the organometallic compound of the formula (I) as defined hereinbefore, wherein X and L are unsubstituted or substituted by one or more substitution groups selected from linear or branched alkyl groups having from one to six carbon atoms unsubstituted or substituted by one or more radicals selected from fluoro or amino.

According to a fourth particular embodiment, the invention is related to the organometallic compound of the formula (I) as defined hereinbefore, wherein X and L are unsubstituted or substituted by one or more substitution groups selected from methyl, ethyl, propyl and butyl, such as the. organo-metallic compound of the formula (I) as defined hereinbefore, wherein L is selected from 1-Methyl-cyclohexadienyl, 2-Methyl-cyclohexadienyl, 3-Methyl-cyclohexadienyl, 6-Methyl-cyclohexadienyl, 1-Ethyl-cyclohexadienyl, 2-Ethyl-cyclohexadienyl, 3-Ethyl-cyclohexadienyl, 6-Ethyl-cyclohexadienyl, 1,6-dimethyl-cyclohexadienyl, 2,6-dimethyl-cyclohexadienyl, 3,6-dimethyl-cyclohexadienyl, 1,6-diethyl-cyclohexadienyl, 2,6-diethyl-cyclohexadienyl, 3,6-diethyl-cyclohexadienyl, 1,6,6-trimethyl-cyclohexadienyl, 2,6,6-trimethyl-cyclohexadienyl, 3,6,6-trimethyl-cyclohexadienyl, 1,6,6-triethyl-cyclohexadienyl, 2,6,6-triethyl-cyclohexadienyl, 3,6,6-triethyl-cyclohexadienyl, 1-Methyl-cycloheptadienyl, 2-Methyl-cycloheptadienyl, 3-Methyl-cycloheptadienyl, 7-Methyl-cycloheptadienyl, 1-Ethyl-cycloheptadienyl, 2-Ethyl-cycloheptadienyl, 3-Ethyl-cycloheptadienyl, 7-Ethyl-cycloheptadienyl, 1,6-dimethyl-cycloheptadienyl, 2,6-dimethyl-cycloheptadienyl, 3,6-dimethyl-cycloheptadienyl, 4,6-dimethyl-cycloheptadienyl, 5,6-dimethyl-cycloheptadienyl, 6,6-dimethyl-cycloheptadienyl, 1,7-dimethyl-cycloheptadienyl, 2,7-dimethyl-cycloheptadienyl, 3,7-dimethyl-cycloheptadienyl, 1,5-dimethyl-cycloheptadienyl, 7,7-dimethyl-cycloheptadienyl, 1,6-diethyl-cycloheptadienyl, 2,6-diethyl-cycloheptadienyl, 3,6-diethyl-cycloheptadienyl, 4,6-diethyl-cycloheptadienyl, 5,6-diethyl-cycloheptadienyl, 6,6-diethyl-cycloheptadienyl, 1,7-diethyl-cycloheptadienyl, 2,7-diethyl-cycloheptadienyl, 3,7-diethyl-cycloheptadienyl, 1,5-diethyl-cycloheptadienyl and 7,7-diethyl-cycloheptadienyl.

According to a fifth particular embodiment, the invention is related to the organometallic compound of the formula (I) as defined hereinbefore, wherein X and L are identical, and still more particularly the following organometallic compounds: Bis(2,6,6-trimethylcyclohexadienyl)ruthenium (Ru(2,6,6-Me$_3$-chxd)$_2$ of the formula:

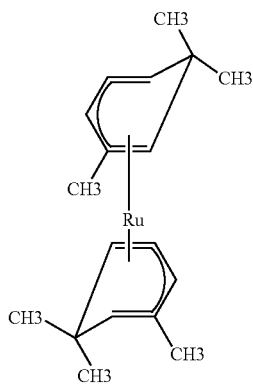

and Bis(methyl-cycloheptadienyl)ruthenium Ru(Me-chpd)$_2$ of the formula:

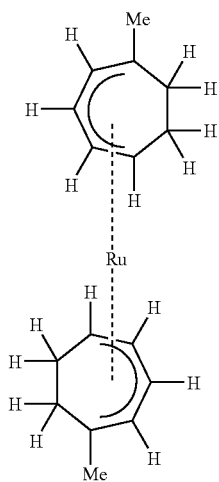

Other examples of organometallic of the formula (I) as defined hereinbefore are:
Ru(1-methyl-cyclohexadienyl)$_2$, Ru(2-methyl-cyclohexadienyl)$_2$,
Ru(3-methyl-cyclohexadienyl)$_2$, Ru(6-methyl-cyclohexadienyl)$_2$,
Ru(1-ethyl-cyclohexadienyl)$_2$, Ru(2-ethyl-cyclohexadienyl)$_2$,
Ru(3-ethyl-cyclohexadienyl)$_2$, Ru(6-ethyl-cyclohexadienyl)$_2$,
Ru(1,6-dimethyl-cyclohexadienyl)$_2$,
Ru(2,6-dimethyl-cyclohexadienyl)$_2$, Ru(3,6-dimethyl-cyclohexadienyl)$_2$,
Ru(1,6-diethyl-cyclohexadienyl)$_2$, Ru(2,6-diethyl-cyclohexadienyl)$_2$,
Ru(3,6-diethyl-cyclohexadienyl)$_2$, Ru(1,6,6-trimethyl-cyclohexadienyl)$_2$,
Ru(2,6,6-trimethyl-cyclohexadienyl)$_2$, Ru(3,6,6-trimethyl-cyclohexadienyl)$_2$,
Ru(1,6,6-triethyl-cyclohexadienyl)$_2$, Ru(2,6,6-triethyl-cyclohexadienyl)$_2$,
Ru(3,6,6-triethyl-cyclohexadienyl)$_2$, Ru(1-methyl-cycloheptadienyl)$_2$,
Ru(2-methyl-cycloheptadienyl)$_2$, Ru(3-methyl-cycloheptadienyl)$_2$,
Ru(7-methyl-cycloheptadienyl)$_2$, Ru(1-ethyl-cycloheptadienyl)$_2$,
Ru(2-ethyl-cycloheptadienyl)$_2$, Ru(3-ethyl-cycloheptadienyl)$_2$,
Ru(7-ethyl-cycloheptadienyl)$_2$, Ru(1,6-dimethyl-cycloheptadienyl)$_2$,
Ru(2,6-dimethyl-cycloheptadienyl)$_2$, Ru(3,6-dimethyl-cycloheptadienyl)$_2$,
Ru(4,6-dimethyl-cycloheptadienyl)$_2$, Ru(5,6-dimethyl-cycloheptadienyl)$_2$,
Ru(6,6-dimethyl-cycloheptadienyl)$_2$, Ru(1,7-dimethyl-cycloheptadienyl)$_2$,
Ru(2,7-dimethyl-cycloheptadienyl)$_2$, Ru(3,7-dimethyl-cycloheptadienyl)$_2$,
Ru(1,5-dimethyl-cycloheptadienyl)$_2$, Ru(7,7-dimethyl-cycloheptadienyl)$_2$,
Ru(1,6-diethyl-cycloheptadienyl)$_2$, Ru(2,6-diethyl-cycloheptadienyl)$_2$,
Ru(3,6-diethyl-cycloheptadienyl)$_2$, Ru(4,6-diethyl-cycloheptadienyl)$_2$,
Ru(5,6-diethyl-cycloheptadienyl)$_2$, Ru(6,6-diethyl-cycloheptadienyl)$_2$,
Ru(1,7-diethyl-cycloheptadienyl)$_2$, Ru(2,7-diethyl-cycloheptadienyl)$_2$,
Ru(3,7-diethyl-cycloheptadienyl)$_2$, Ru(1,5-diethyl-cycloheptadienyl)$_2$, and
Ru(7,7-diethyl-cycloheptadienyl)$_2$.

It can be emphasize that in these compounds, and more generally in the organo-metallic compound of the formula (I), as defined hereinbefore, the distribution of the ligand, together with the configuration of the cyclic carbon molecules and their respective open electronic cloud, optimize the steric hindrance and the reduction of the electronic interaction, which is believed to help to decrease their melting point. According to a second embodiment, the invention relates to a process for the preparation of the compound as hereinbefore defined comprising the reaction of Ru$^{+++}$ salt with the appropriate organic ligand in the presence of Zinc.

According to a third embodiment, the invention relates to a process for the preparation of the compound as hereinbefore defined, comprising the reaction of di-µ-chlorodichloro bis [(1-3η:6-8η)-2,7-dimethyl-octadienyl]diruthenium in LiCO$_3$ with a solution of ethanol containing the appropriate ligand and acetonitrile.

According to a fourth embodiment, the invention relates to a process for the deposition of a ruthenium containing film on a substrate, comprising the steps of:
 a)—Providing at least one substrate into a reactor;
 b)—Introducing into the said reactor at least one organometallic compound of the formula (I), as defined hereinbefore,
 c)—Decomposing or adsorbing on the substrate(s) said at least one organo-metallic compound into the said reactor set at a temperature equal or higher than 100° C.;
 d)—Depositing said ruthenium containing film onto said at least one substrate.

In the process as defined hereinbefore, the various reactants can be introduced into the reactor either simultaneously such as in CVD, sequentially such as in ALD or in different combinations thereof.

Accordingly, the ruthenium containing precursors defined in step b) here hereinbefore shall be usually liquids, in other words having a melting point below 20° C., and more preferably shall have a melting point below 0° C.

In the process as defined hereinbefore, the substrate is generally chosen from the usual oxides which are used to manufacture metal electrodes such as MIM, DRAM, gate dielectrics or capacitors, as silicon oxide, Germanium oxides and the like.

In the process as defined hereinbefore, the temperature conditions are selected into a range from 100° C. to 500° C., more preferably from 150° C. to 350° C. and the pressure into the reactor shall be preferably maintained between 1 Pa and $10^5$ Pa, more preferably between 25 Pa and $10^3$ Pa.

According to a first particular embodiment of the process as defined hereinbefore it further comprises a step of:

e)—Providing at least one reducing fluid into the reactor.

As examples of reducing fluids used in step e) of the process as defined hereinbefore, are more particularly $H_2$, $NH_3$, $SiH_4$, $Si_2H_6$, $Si_3H_8$, hydrogen containing fluids or mixtures thereof.

According to a second particular embodiment of the process as defined hereinbefore, it further comprises a step of:

f)—Providing at least one oxygen containing fluid into the reactor.

As examples of oxygen containing fluids used in step f) of the process as defined hereinbefore, are more particularly $O_2$, $O_3$, $H_2O$, $H_2O_2$, oxygen containing radicals such as $0°$ or OH ° or mixtures thereof.

In the process as defined hereinbefore and further comprising a step e) and/or a step f), the hydrogen-containing and/or oxygen-containing fluid may be continuously introduced in the reactor and the organometallic compound or the mixture of organometallic compounds may be applied on the substrate by pulse such as according to the technique of pulsed chemical vapor deposition (PCVD).

Depending on the reactants and the experimental conditions, the process defined as hereinbefore, allow the formation of, either ruthenium metallic film, ruthenium oxide or ruthenium-containing film.

Figure 2:
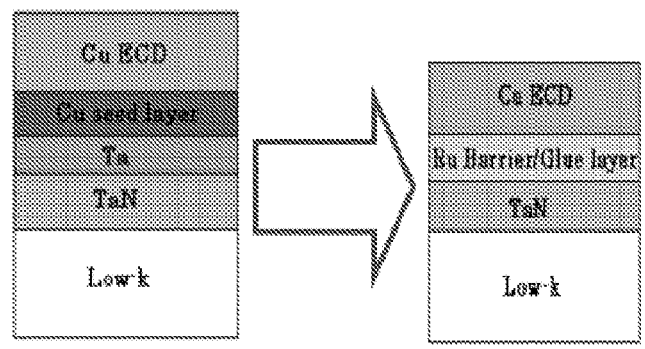

As illustrations of some various examples, FIG. 1 is a schematic representation of a Complementary Metal Oxide Semi-conductor CMOS structure, where Ru is used and FIG. 2 is a schematic representation of a stacking structure for barrier layers between copper wires and the isolating layers (called low-k and usually made of porous silicon oxycarbide).

According to a last embodiment, the invention relates to the use of an organo-metallic compound as hereinbefore defined or of a mixture thereof, as a ruthenium precursor to manufacture ruthenium based film coated metal electrodes. Such devices are mainly used in the electronic industry.

EXAMPLES OF PREPARATION OF COMPOUNDS ACCORDING TO THE FORMULA (I)

Example 1 bis(2,6,6-trimethyl-cyclohexadienyl)ruthenium

Anhydrous trichloride ruthenium ($RuCl_3.nH_2O$) in ethanol is mixed with zinc (Zn) dust and 2,6,6-trimethyl-cyclohexadiene.

The mixture is heated under reflux and then filtered. The resulting solution is evaporated in vacuo to dryness, extracted with n-pentane, and filtered through alumina. The resulting solution is then cooled to −78 C to give the final product.

Example 2 bis(1-methyl-cycloheptadienyl)ruthenium

Anhydrous trichloride ruthenium ($RuCl_3.nH_2O$) in ethanol is mixed with zinc (Zn) dust and 2-methyl-1,3-cycloheptadiene.

The mixture is heated under reflux and then filtered. The resulting solution is evaporated in vacuo to dryness, extracted with n-pentane, and filtered through alumina. The resulting solution is then cooled to −78 C to give the final product.

Example 3

(2,6,6-trimethyl-cyclohexadienyl)(1-3η:6-8η)-2,7-dimethyloctadienyl)ruthenium

A slurry of di-μ-chlorodichlorobis[(1-3η:6-8η)-2,7-dimethyloctadienyl]diruthenium in lithium carbonate ($LiCO_3$) is mixed with a solution of ethanol containing 2,6,6-trimethyl-cyclohexadiene and acetonitrile, ($CH_3CN$). The mixture is refluxed and the solvent is evaporated under vacuum and the residues stirred. The resulting solution is chromatographed on alumina. The final elution step with hexane, results in the product in fairly good yield.

Example 4

(1-methyl-cycloheptadienyl)(1-3η:6-8η)-2,7-dimethyloctadienyl)ruthenium

A slurry of di-μ-chlorodichlorobis[(1-3η:6-8η)-2,7-dimethyloctadienyl]diruthenium in lithium carbonate ($LiCO_3$) is mixed with a solution of ethanol containing 2-methyl-1,3-cycloheptadiene and acetonitrile, ($CH_3CN$). The mixture is refluxed and the solvent is evaporated under vacuum and the residues stirred. The resulting solution is chromatographed on alumina. The final elution step with hexane, results in the product in fairly good yield.

Examples of Depositions of ruthenium Films Under Different Operating Conditions Using bis(2,6,6-trimethyl-cyclohexadienyl)Ruthenium Ru(2,6,6-trimethyl-cyclohexadienyl)$_2$ is a light yellow precursor, which is liquid at 20° C.

Deposition of Pure ruthenium Films:

Pure ruthenium films were deposited from temperatures above 250° C. using bis(2,6,6-trimethyl-cyclohexadienyl)ruthenium. The liquid precursor was stored in a bubbler heated up at 80° C. and whose vapors were delivered to the hot-wall reactor by a bubbling method. An inert gas, helium in this case, was used as a carrier gas, as well as for dilution purpose. Tests were done with and without hydrogen as co-reactant.

With the conditions of our set-up, films were deposited from 250° C., at 0.5 Torr, and the deposition rate reached a plateau at 350° C. Depositions were done on silicon oxide. The concentration of various elements into the ruthenium films, were analyzed by an Auger spectrometer. Pure ruthenium films were deposited onto a thermal silicon dioxide layer. The concentration of oxygen in the ruthenium film was below the detection limit of AES.

Atomic Layer Deposition:

This precursor bis(2,6,6-trimethyl-cyclohexadienyl)ruthenium is suitable for the atomic layer deposition (ALD) of ruthenium films at low temperatures (150-350° C.) using the appropriate co-reactant. It has been found that metallic ruthenium depositions in ALD technique are possible when the co-reactant is molecular and atomic hydrogen, as well as with ammonia and related radicals $NH_2$, NH, and oxidants.

Deposition of Ruthenium Oxide Films:

Ruthenium oxide films were deposited by making bis(2,6,6-trimethyl cyclohexadienyl)ruthenium and an oxygen containing fluid react in a deposition furnace. In this particular case, the oxygen containing fluid was oxygen. It has been found that ruthenium oxide depositions in ALD technique are possible when the co-reactant is molecular and atomic oxygen, as well as moisture vapors or any other oxygen containing mixture.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A process for the deposition of a ruthenium containing film on a substrate, comprising the steps of:
    a) providing at least one substrate into a reactor;
    b) introducing into the said reactor at least one organo-metallic compound of the formula (I):

L-Ru—X         (I)

wherein:
    L is a non-aromatic cyclic unsaturated hydrocarbon ligand (L), having at least six cyclic carbon atoms, said cycle being unsubstituted or substituted by one or more substitution groups selected from linear or branched alkyl groups having from one to six carbon atoms unsubstituted or substituted by one or more radicals selected from fluoro, hydroxy or amino, linear or branched alkylamide groups having from one to six carbon atoms, linear or branched alkoxy groups having from one to six carbon atoms, linear or branched alkyl amidinates having from one to six carbon atoms, and
    X is either a non aromatic cyclic unsaturated hydrocarbon ligand identical or different from (L), having at least six cyclic carbon atoms said cycle being unsubstituted or substituted by one or more substitution groups selected from linear or branched alkyl groups having from one to six carbon atoms unsubstituted or substituted by one or more radicals selected from fluoro, hydroxy or amino, linear or branched alkylamide groups having from one to six carbon atoms, linear or branched alkoxy groups having from one to six carbon atoms, linear or branched alkyl amidinates having from one to six carbon atoms, or a cyclic or acyclic conjugated alkadienyl hydrocarbon ligand having from five to ten carbons atoms, said hydrocarbon ligand being unsubstituted or substituted by one or more substitution groups selected from linear or branched alkyl groups having from one to six carbon atoms unsubstituted or substituted by one or more radicals selected from fluoro, hydroxy or amino, linear or branched alkylamides group having from one to six carbon atoms, linear or branched alkoxy groups having from one to six carbon atoms, linear or branched alkyl amidinates having from one to six carbon atoms;
    c) decomposing or adsorbing on the substrate(s) said at least one organo-metallic compound into the said reactor set at a temperature equal or higher than 100° C.; and
    d) depositing said ruthenium containing film onto said at least one substrate.

2. The process of claim 1, further comprising a step e) of providing at least one reducing fluid into the reactor, together with the at least one ruthenium precursor or separately.

3. The process of claim 1, further comprising a step f) of providing at least one oxygen containing fluid into the reactor, together with the at least one ruthenium precursor or separately.

4. The process of claim 2, further comprising a step f) of providing at least one oxygen containing fluid into the reactor, together with the at least one ruthenium precursor or separately.

5. The process of claim 1, wherein, in the organometallic compound of formula (I), (L) is selected from cyclohexadienyl (hereafter chxd, $C_6H_7$) and cycloheptadienyl (hereafter chpd $C_7H_9$) ligands, said ligands being unsubstituted or substituted by one or more substitution groups selected from linear or branched alkyl groups having from one to six carbon atoms unsubstituted or substituted by one or more radicals selected from fluoro, hydroxy or amino, linear or branched alkylamides group having from one to six carbon atoms, linear or branched alkoxy groups having from one to six carbon atoms, linear or branched alkyl amidinates having from one to six carbon atoms, or a cyclic or acyclic conjugated alkadienyl hydrocarbon ligand having from five to ten carbons atoms, said hydrocarbon ligand being unsubstituted or substituted by one or more substitution groups selected from linear or branched alkyl groups having from one to six carbon atoms unsubstituted or substituted by one or more radicals selected from fluoro, hydroxy or amino, linear or branched alkylamide groups having from one to six carbon atoms, linear or branched alkoxy groups having from one to six carbon atoms, linear or branched alkyl amidinates having from one to six carbon atoms.

6. The process of claim 1, wherein, in the organometallic compound of formula (I), X is selected from cyclohexadienyl (hereafter chxd, $C_6H_7$), cycloheptadienyl (hereafter chpd $C_7H_9$), cyclopentadienyl, pentadienyl, hexadienyl and heptadienyl ligands, said ligands being unsubstituted or substituted by one or more substitution groups selected from linear or branched alkyl groups having from one to six carbon atoms unsubstituted or substituted by one or more radicals selected from fluoro, hydroxy or amino, linear or branched alkylamide groups having from one to six carbon atoms, linear or branched alkoxy groups having from one to six carbon atoms, linear or branched alkyl amidinates having from one to six carbon atoms.

7. The process of claim 1, wherein, in the organometallic compound of formula (I), X and L are unsubstituted or substituted by one or more substitution groups selected from linear or branched alkyl groups having from one to six carbon atoms unsubstituted or substituted by one or more radicals selected from fluoro or amino.

8. The process of claim 1, wherein, in the organometallic compound of formula (I), X and L are unsubstituted or substituted by one or more substituting groups selected from methyl, ethyl, propyl and butyl.

9. The process of claim 1, wherein, in the organometallic compound of formula (I), L is selected from 1-Methyl-cyclohexadienyl, 2-Methyl-cyclohexadienyl, 3-Methyl-cyclohexadienyl, 6-Methyl-cyclohexadienyl, 1-Ethyl-cyclohexadienyl, 2-Ethyl-cyclohexadienyl, 3-Ethyl-cyclohexadienyl, 6-Ethyl-cyclohexadienyl, 1,6-dimethyl-cyclohexadienyl, 2,6-dimethyl-cyclohexadienyl, 3,6-dimethyl-cyclohexadienyl, 1,6-diethyl-cyclohexadienyl, 2,6-diethyl-cyclohexadienyl, 3,6-diethyl-cyclohexadienyl, 1,6,6-trimethyl-cyclohexadienyl, 2,6,6-trimethyl-cyclohexadienyl, 3,6,6-trimethyl-cyclohexadienyl, 1,6,6-triethyl-cyclohexadienyl, 2,6,6-triethyl-cyclohexadienyl, 3,6,6-triethyl-cyclohexadienyl, 1-Methyl-cycloheptadienyl, 2-Methyl-cycloheptadienyl, 3-Methyl-cycloheptadienyl, 7-Methyl-cycloheptadienyl, 1-Ethyl-cycloheptadienyl, 2-Ethyl-cycloheptadienyl, 3-Ethyl-cycloheptadienyl, 7-Ethyl-cycloheptadienyl, 1,6-dimethyl-cycloheptadienyl, 2,6-dimethyl-cycloheptadienyl, 3,6-dimethyl-cycloheptadienyl, 4,6-dimethyl-cycloheptadienyl, 5,6-dimethyl-cycloheptadienyl, 6,6-dimethyl-cycloheptadienyl, 1,7-dimethyl-cycloheptadienyl, 2,7-dimethyl-cycloheptadienyl, 3,7-dimethyl-cycloheptadienyl, 1,5-dimethyl-cycloheptadienyl, 7,7-dimethyl-cycloheptadienyl, 1,6-diethyl-cycloheptadienyl, 2,6-diethyl-cycloheptadienyl, 3,6-diethyl-cycloheptadienyl, 4,6-diethyl-cycloheptadienyl, 5,6-diethyl-cycloheptadienyl, 6,6-diethyl-cycloheptadienyl, 1,7-diethyl-cycloheptadienyl, 2,7-diethyl-cycloheptadienyl, 3,7-diethyl-cycloheptadienyl, 1,5-diethyl-cycloheptadienyl and 7,7-diethyl-cycloheptadienyl.

10. The process of claim 1, wherein, in the organo-metallic compound of formula (I), wherein X and L are identical.

11. The process of claim 1, wherein the organometallic compound of formula (I) are:
Bis(2,6,6-trimethylcyclohexadienyl) ruthenium;
Bis(methyl-cycloheptadienyl) ruthenium;
(2,6,6-trimethyl-cyclohexadienyl) (1-3η:6-8η)-2,7-dimethyloctadienyl) ruthenium; or
(1-methyl-cycloheptadienyl) (1-3η:6-8η)-2,7-dimethyloctadienyl) ruthenium.

* * * * *